(12) United States Patent
Folk

(10) Patent No.: US 11,635,477 B2
(45) Date of Patent: Apr. 25, 2023

(54) CONTINUOUS ONBOARD RE-CHARGE ENVIRONMENT

(71) Applicant: Raymond Folk, Niceville, FL (US)

(72) Inventor: Raymond Folk, Niceville, FL (US)

( * ) Notice: Subject to any disclaimer, the term of this patent is extended or adjusted under 35 U.S.C. 154(b) by 0 days.

(21) Appl. No.: 17/357,918

(22) Filed: Jun. 24, 2021

(65) Prior Publication Data
US 2021/0339639 A1 Nov. 4, 2021

Related U.S. Application Data

(60) Provisional application No. 62/705,439, filed on Jun. 26, 2020.

(51) Int. Cl.
| | |
|---|---|
| *B60L 53/22* | (2019.01) |
| *G01R 33/28* | (2006.01) |
| *A61K 49/10* | (2006.01) |
| *G01R 33/56* | (2006.01) |
| *H02J 7/35* | (2006.01) |

(52) U.S. Cl.
CPC ............ *G01R 33/282* (2013.01); *A61K 49/10* (2013.01); *B60L 53/22* (2019.02); *G01R 33/5601* (2013.01); *B60L 2210/20* (2013.01); *H02J 7/35* (2013.01)

(58) Field of Classification Search
CPC .. G01R 33/282; G01R 33/5601; A61K 49/10; B60L 53/22; B60L 2210/20; H02J 7/35; Y02T 10/70; Y02T 10/7072; Y02T 90/14

USPC .......................................................... 320/104
See application file for complete search history.

(56) References Cited

U.S. PATENT DOCUMENTS

| | | | |
|---|---|---|---|
| 4,597,463 A | 7/1986 | Barnard | |
| 8,866,438 B2 * | 10/2014 | Lee ......................... | B60L 53/22 320/109 |
| 9,656,657 B2 | 5/2017 | Gibson | |
| 10,569,638 B2 | 2/2020 | Welschoff | |
| 10,632,851 B2 | 4/2020 | Münning | |
| 2003/0184152 A1 | 10/2003 | Cikanek | |
| 2011/0198143 A1 | 8/2011 | Gravino | |
| 2014/0012443 A1 | 9/2014 | Bolenbaugh | |
| 2014/0253018 A1 * | 9/2014 | Kong ...................... | B60L 53/22 320/104 |

* cited by examiner

*Primary Examiner* — Paul Dinh
(74) *Attorney, Agent, or Firm* — Baker Donelson (57) ABSTRACT

An article of manufacture for providing an onboard vehicle recharging environment according to the present invention is disclosed. A Continuous Onboard Recharging Environment (CORE) translates mechanical rotational energy obtained from the rotating axles of a vehicle to a form of sufficient voltage and load amperage to facilitate the charging of an Electric Vehicle's battery system while the vehicle is in operation, thus reducing or removing the need for external charging.

10 Claims, 7 Drawing Sheets

CONTINUOUS ONBOARD RE-CHARGE ENVIRONMENT

CROSS-REFERENCE TO RELATED APPLICATION

This application claims priority to U.S. Provisional Patent Application No. 62/705,439, titled "Portable Charging system for Electric Vehicles," and filed on Jun. 26, 2020. The entire application is incorporated herein by reference in its entirety.

TECHNICAL FIELD

This application relates in general to an article of manufacture for providing vehicle energy devices, and more specifically, to an article of manufacture providing an onboard vehicle recharging environment.

BACKGROUND

One major drawback that currently exists in the market today, is the slow progress of federal, state and local agencies to build and sufficiently maintain an infrastructure that can and would support a dramatic increase in alternative fuel-sourced vehicles, especially electric vehicles (EVs). It has been left to individual outlet and retail environments to provide such amenities and capabilities.

A secondary deficiency is for electric vehicle manufacturers to be able to offer a "comparable" cost-effective alternative to combustion engine vehicles, due to their more limited driving distance restrictions. This factor limits the EV's ability to operate as long as or as far as a standard vehicle, without a "long" period of rest required to recharge.

Current methodology and design uses a portion of the vehicle's main battery assembly to provide the recharging voltages; this approach, however, leads to substantial deficiencies in overall performance.

Therefore, a need exists for an article of manufacture for providing an onboard vehicle recharging environment. The present invention attempts to address the limitations and deficiencies in prior solutions according to the principles and example embodiments disclosed herein.

SUMMARY

In accordance with the present invention, the above and other problems are solved by providing an article of manufacture for an onboard vehicle recharging environment according to the principles and example embodiments disclosed herein.

In one embodiment, the present invention is an article of manufacture for providing an onboard vehicle recharging environment. The onboard vehicle recharging environment includes a voltage generator coupled by a mechanical device to rotating axle in a vehicle, the voltage generator generates a 12 VAC signal, one or more voltage conversion signal path stages for converting the 12 VAC signal to an output power signal for coupling to a vehicle onboard battery recharging assembly, a memory having instructions stored thereon, and a control center processor having a processor configured to execute the instructions on the memory to cause the electronic onboard vehicle recharging environment to operate is a plurality of operating modes. The operating modes include an Off Mode, an On Mode, an Auto Mode, and a Soler/EM Mode.

In another aspect of the present invention, the one or more voltage conversion signal path stages generate the output power signal for charging the vehicle onboard battery including a 120 VAC signal, a 230 VAC signal, a 240 VAC signal, a 200 VDC signal, and a 400 VDC signal.

In another aspect of the present invention, the onboard vehicle recharging environment further comprises a clutch device between the voltage generator and the mechanical device coupled to the vehicle axle.

In another aspect of the present invention, the mechanical device comprises one of the following: a belt/pully connection to a vehicle transaxle, a belt/pully connection to a vehicle driveshaft; a direct connection to a vehicle transaxle, and a direct connection to a vehicle driveshaft.

In another aspect of the present invention, the off mode disengages the clutch to shut down the output power signal from the voltage generator.

In another aspect of the present invention, the off mode keeps the powered and online to allowing for operation when the operating mode changes.

In another aspect of the present invention, the on mode is the default mode for vehicles that are not equipped with a secondary battery package a solar panels, and an auxiliary input device.

In another aspect of the present invention, the auto mode is used as the default mode if vehicle is equipped with either a Secondary Battery Array, Solar Panels, or other auxiliary device input.

In another aspect of the present invention, the Solar/EM Mode is used for driving or traffic situations where the vehicle encounters slower than normal driving, numerous stop-and-go conditions and heavily congested city driving conditions.

In another aspect of the present invention, the vehicle comprises a hybrid electrical-combustion engine and an electrical vehicle.

The foregoing has outlined rather broadly the features and technical advantages of the present invention in order that the detailed description of the invention that follows may be better understood. Additional features and advantages of the invention will be described hereinafter that form the subject of the claims of the invention.

It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Referring now to the drawings in which like reference numbers represent corresponding parts throughout.

DETAILED DESCRIPTION

This application relates in general to an article of manufacture for providing vehicle energy devices, and more specifically, to an article of manufacture providing an onboard vehicle recharging environment according to the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In describing embodiments of the present invention, the following terminology will be used. The singular forms "a," "an," and "the" include plural referents unless the context clearly dictates otherwise. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. As used herein, the singular forms "a," "an," and "the" are intended to include the plural forms as well, unless the context clearly indicates otherwise.

It further will be understood that the terms "comprises," "comprising," "includes," and "including" specify the presence of stated features, steps or components, but do not preclude the presence or addition of one or more other features, steps or components. It also should be noted that in some alternative implementations, the functions and acts noted may occur out of the order noted in the figures. For example, two figures shown in succession may in fact be executed substantially concurrently or may sometimes be executed in the reverse order, depending upon the functionality and acts involved.

The terms "individual" and "user" refer to an entity, e.g., a human, using an article of manufacture providing an onboard vehicle recharging environment according to the present invention. The term user herein refers to one or more users.

The term "invention" or "present invention" refers to the invention being applied for via the patent application with the title "Continuous Onboard Recharging Environment." Invention may be used interchangeably with recharger.

Figure 1:
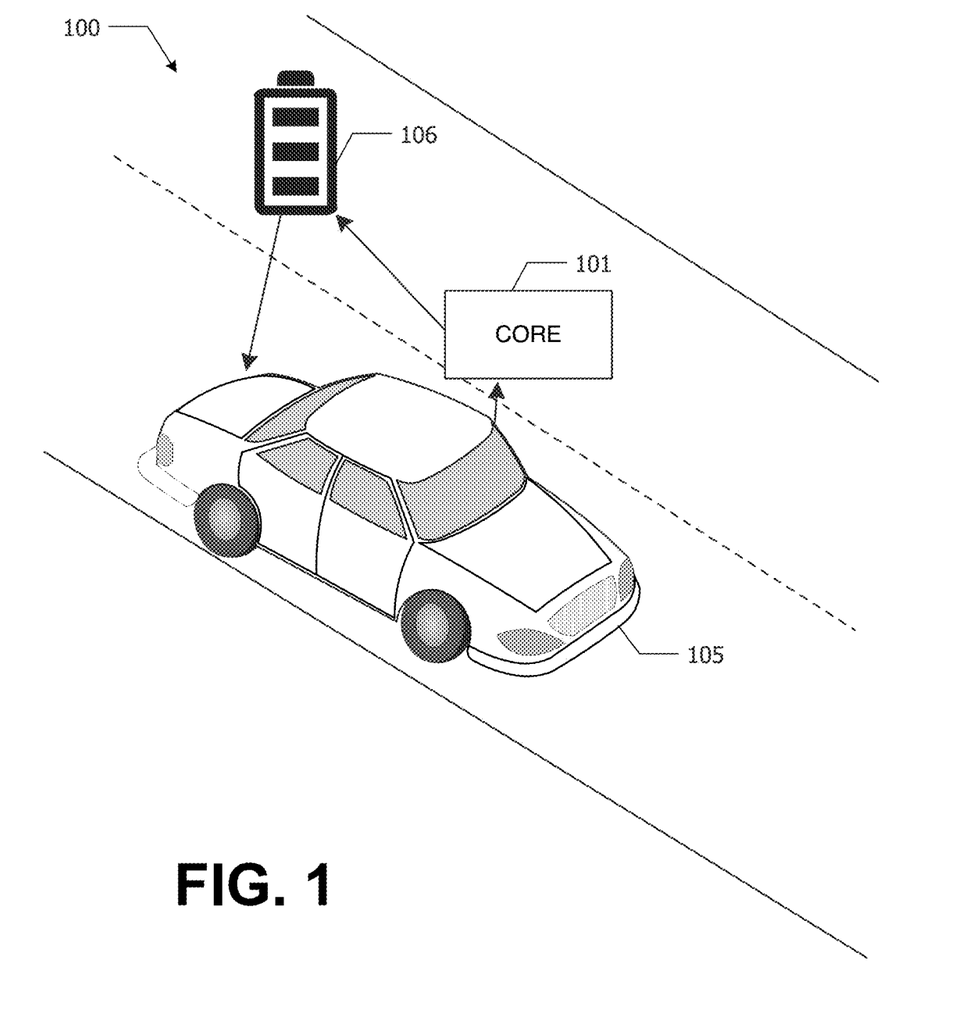
FIG. 1 illustrates an example embodiment of an article of manufacture providing an onboard vehicle recharging environment according to the present invention.

In general, the present disclosure relates to an article of manufacture providing an onboard vehicle recharging environment according to the present invention. To better understand the present invention, FIG. 1 illustrates an example embodiment of an article of manufacture providing an onboard vehicle recharging environment according to the present invention. An electric or hybrid vehicle 105 contains a Continuous Onboard Re-Charging Environment (CORE. component 101 that is integrated into the vehicle's drivetrain to extend the range of the EV 105 by adding electrical charge to the vehicle batteries 106 as the vehicle 105 drives down the road.

A CORE system 100 is a portable, onboard continuous charging capable technology, for EVs 105, primarily targeting vehicles used for medium- and long-range driving or transportation. The CORE system 100 is also adaptable to mainstream EVs as well. This technology also can be implemented in "standard scenario" driving on full-electric and hybrid-electric vehicles that may be used for occasional long-range driving or transportation, such as vacation travel. CORE technology is targeted toward situations where the majority of vehicle driving distances exceeds 50 miles or where long-haul transportation is expected, but also is easily adaptable to every-day electric vehicle driving scenarios. These "standard" driving scenarios will benefit from CORE if the vehicle is used to drive in excess of 50 miles at any given time, with the ability to turn the system off or on when necessary. This allows for the same benefits as medium and long-distance vehicles, but only when needed. This technology is designed for fully electric vehicles but can easily be adapted to hybrid-electric vehicles and is designed to cover both new design and aftermarket add-on installation kits.

The CORE system 100 is a technology designed to be integrated with or into current existing fully-electric or hybrid-electric vehicles 104 or future design technology, to provide vehicle operational drive time and distance expansion, depending on the driving environment. The CORE system 100 is intended to provide a constant and steady charging voltage to allow charging of the existing battery system, while the vehicle is in motion, without the inefficiency and drawbacks of expending or using any of the vehicle's battery voltage to produce the recharging voltages. It is designed to replicate the input charging energy as if the vehicle were parked and connected to an external charging system.

This result is accomplished by generating mechanical-to-electrical energy and amplifying and regulating the energy as necessary to achieve ample charge voltage levels, the output voltage of the CORE device, and direct that charging voltage to the vehicle's existing charge port connection to allow battery charging through the vehicle's equipped onboard charging system. Use of CORE on a vehicle can dramatically extend the driving range of electric vehicles, with minimal cost and impact to current vehicle design or abilities and without impacting current design methodologies. Use of CORE can provide sufficient and sustained charging voltages, without the inefficiency and drawbacks of using and converting onboard battery power to produce such charging voltages. Use of CORE can drastically reduce the dependency on fossil fuels, whether petroleum or natural gas. Use of CORE can dramatically reduce the overall toxic carbon emissions produced by combustion automobiles, thus reducing toxic greenhouse gasses.

Additionally, use of CORE can reduce the vehicle's carbon footprint to nearly zero while dramatically extending the range of those vehicles; can reduce the overall transportation and travel costs of transporting goods over long distances by reducing the operational costs associated with current delivery methodologies; can allow for drastic reduction in costs for individual or family travel, by reducing the dependency on "fuel" expenses, especially when exceeding 50 miles or more; and can reduce the frequency of stops or "down time" to enable recharging of the vehicle's battery system thereby reducing the vehicle's dependency on charging services and locations with limited availability. This technology system is not intended to replace a home or external charging system environment, but to supplement and extend the overall driving range of these vehicles and reduce the dependency on both home and commercial charging station infrastructure while reducing the need for periodic stopping and charging of the vehicle.

Figure 2:
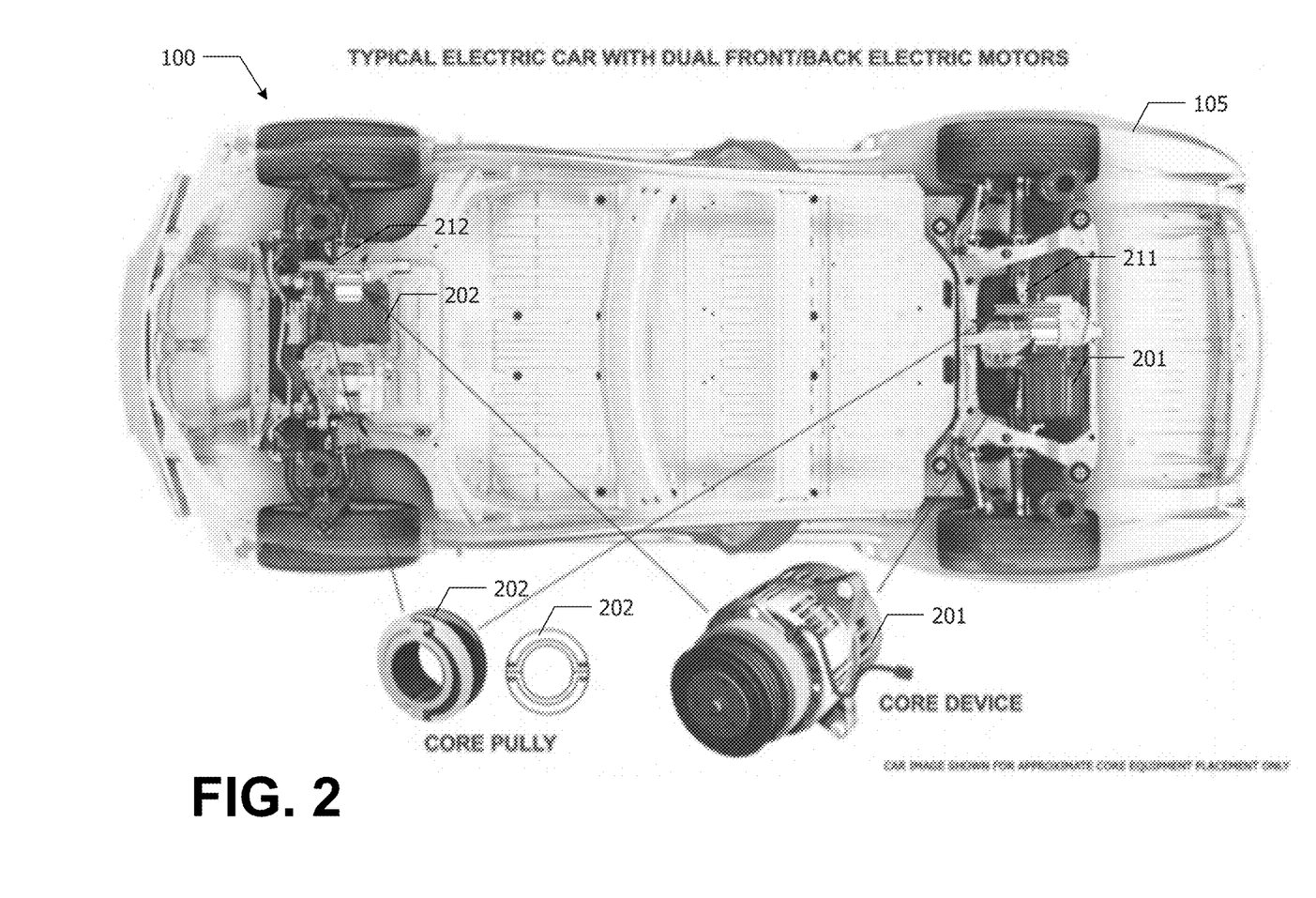
FIG. 2 illustrates an article of manufacture installed on a vehicle for providing an onboard vehicle recharging environment according to the present invention.

FIG. 2 illustrates an article of manufacture installed on a vehicle 105 for providing an onboard vehicle recharging environment according to the present invention. The CORE system 100 generates mechanical-to-electrical energy and amplifies and regulates the energy, as necessary, to achieve ample charge voltage levels, the output voltage of the CORE device, and direct that charging voltage to the vehicle's existing charge port connection to allow battery charging through the vehicle's equipped on-board charging system.

Mechanical to electrical "rotational" energy or voltage is produced by the CORE 101, which is a clutch-activated generator type device 201, being attached to either the transaxle or the driveshaft, via either a belt/pully connection 202 or direct connection to the transaxle, driveshaft or transmission. The CORE connection 101 can be made at either the front or the rear axles of the vehicle as its only requirement is to be connected to an inline rotational "non-steering" shaft of sufficient rotational speed to produce the required voltages. The CORE device 201 should be mounted either near the selected rotational axle 211, via a stable and secure mounting bracket assembly and attached to the axle 212 via a belt attached to an installed pully device 202, or by direct connection to either the electric motor or transmission assemblies.

As the vehicle 105 drives down a roadway, the CORE device 201 captures the rotational energy of the axles 211-212 to generate electrical energy that may be returned to the vehicle battery 106. As such, energy that is otherwise wasted may be captured and reused to extend the range of the vehicle 105.

Figure 3A:
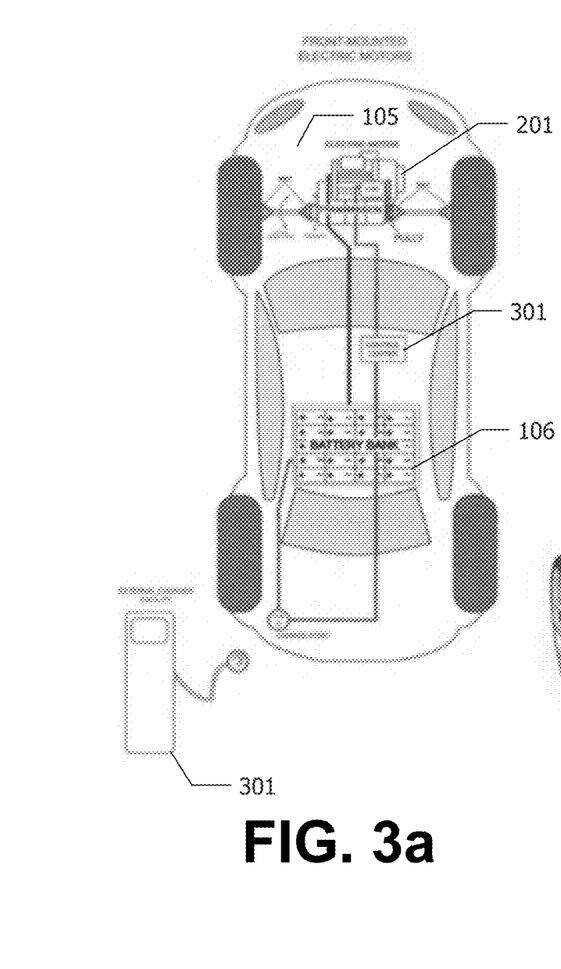
FIGS. 3a-c illustrate embodiments of an article of manufacture installed on vehicles for providing an onboard vehicle recharging environment according to the present invention.
Figures 3B, 3C:
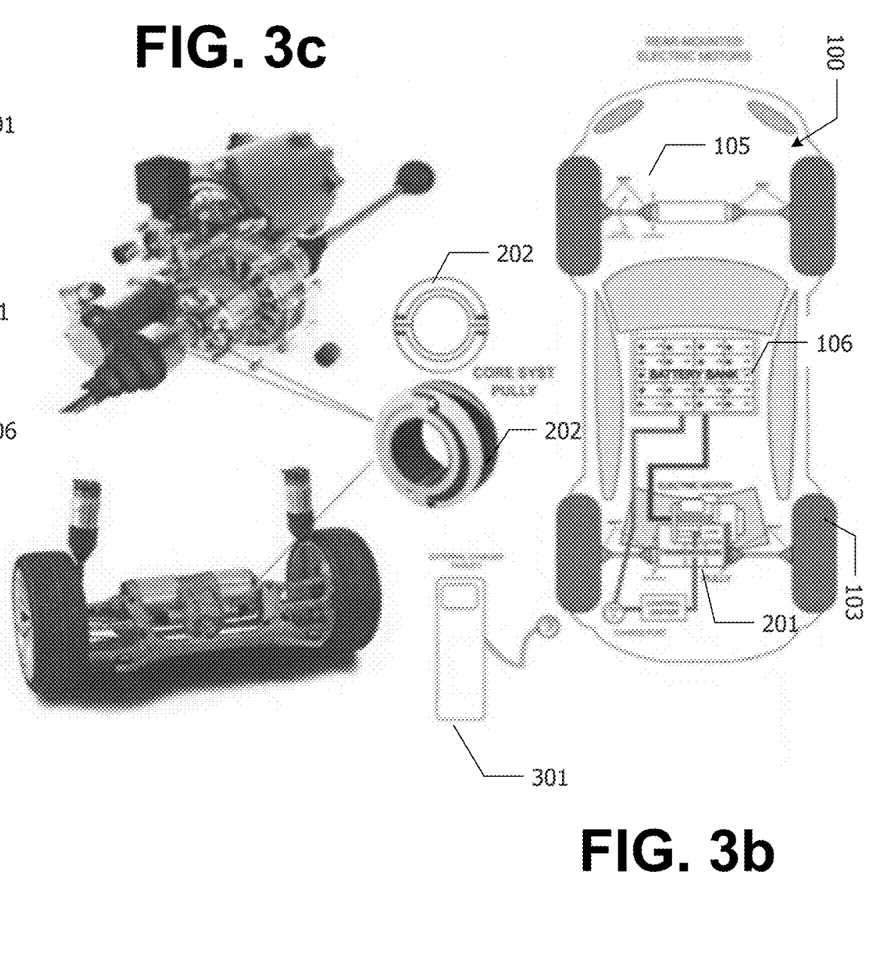

FIGS. 3a-c illustrate embodiments of an article of manufacture installed on vehicles for providing an onboard vehicle recharging environment according to the present invention. FIG. 3a shows a CORE device 201 coupled to a front axle 311 of a vehicle 305a. Similarly, FIG. 3b shows a CORE device 201 coupled to a rear axle 312 of a vehicle 305b. FIG. 3c shows close up views of the CORE device 201 in the vehicles 305a-b. In both FIGS. 3a-b, the CORE device 201 is electrically coupled to the battery 106.

The CORE device 201 translates mechanical rotational energy to a form of sufficient voltage and load amperage to facilitate the charging of an EV's battery system while the vehicle is in operation, thus limiting or removing the need for external charging. Mechanical (rotational) to electrical energy in the form of a voltage is produced by the CORE (generator-type) device being attached to either the transaxle or the driveshaft, via either a belt/pully connection or direct connection to the transaxle, driveshaft or transmission. As the axle, driveshaft or transmission rotates for vehicle movement, the CORE device 201 produces a voltage that is then either conditioned or rectified internally or is then passed to the Control Center Module (CCM) 301, where it is further conditioned in the regulator or booster subsystems. The operation of the various embodiments of the CORE device 201 are described in more detail with respect to FIGS. 4-5 below.

Voltage regulation and conditioning is accomplished by the CCM 301 to provide a somewhat stable charging voltage regardless of generator rotational speed. The boosted or amplified voltages are then passed to the vehicle's existing onboard charging system, to supply a continuous charging voltage, as long as the vehicle is in motion. The CCM module 301 interfaces with both the vehicle's original equipment manufacturer (OEM) equipment and the proposed CORE component 201 subsystems, and conditions and amplifies as necessary the DC and AC voltage and current generated by the mechanically connected generator device to provide a sufficient charging voltage for input to the vehicle's existing onboard charging system to provide auxiliary charging of the battery in use, thus prolonging the battery charge duration time and extending the vehicle's driving range. As noted above, the CORE device 201 may be connected to the vehicle axles 211-212 by a pully 202 or a direct connection.

The CCM module 301 senses, monitors, regulates, and amplifies voltages being fed from the CORE device 201 as well as conditions and amplifies all auxiliary input signals, either from the existing control system or from after-market auxiliary add-on devices, such as solar panels. Monitoring is accomplished via charge status indicators on a Status Indicator Console, showing the percentage of dissipation or charging, as well as indication of proper sub system operation.

Figure 4:
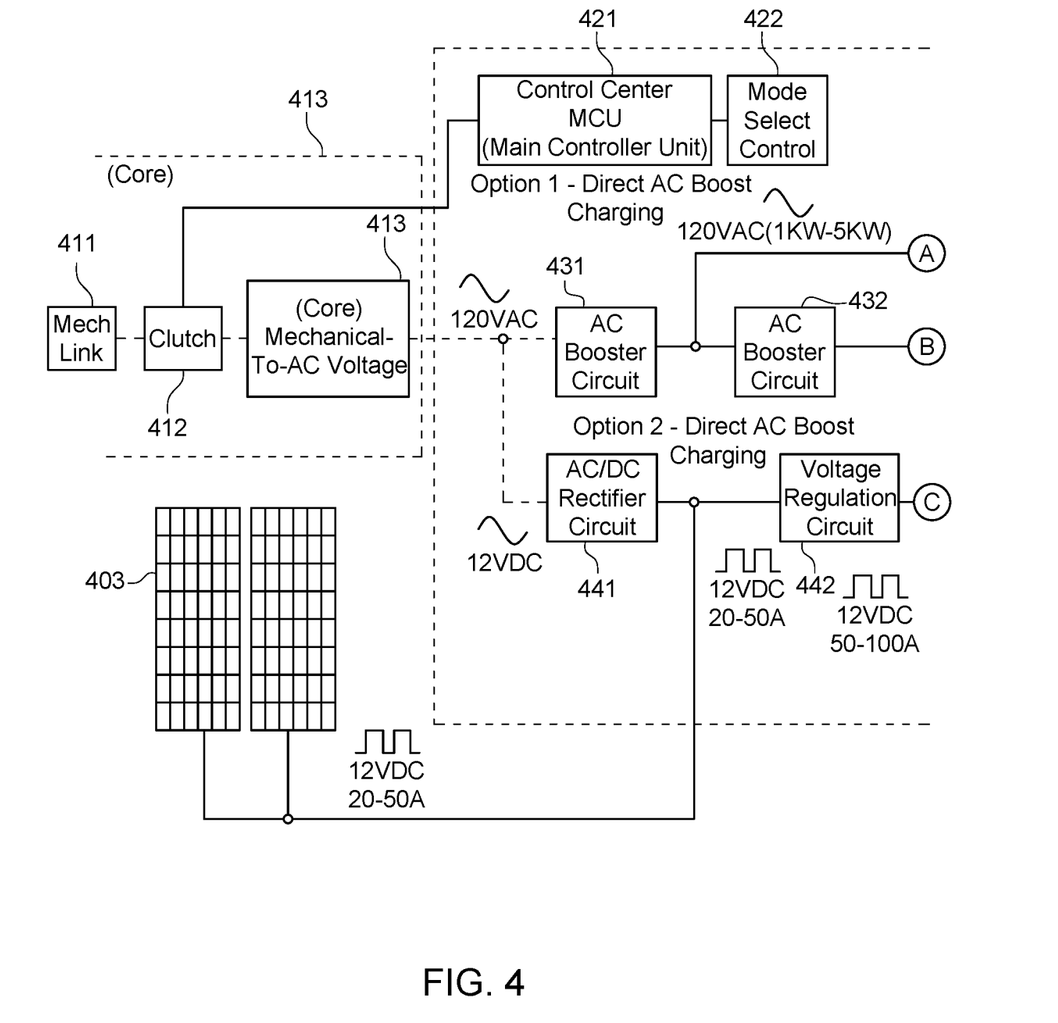
FIG. 4 illustrates a block diagram of electrical components within an article of manufacture providing an onboard vehicle recharging environment according to the present invention.

FIG. 4 illustrates a block diagram of electrical components within an article of manufacture providing an onboard vehicle recharging environment according to the present invention. FIG. 4 shows a first embodiment of a CORE system 100 that utilizes direct AC boost charging. Direct AC boost charging is when mechanical to electrical energy is produced by the CORE 413 providing low voltage AC sinewaves via rotational mechanical linkage 411 via a clutch 412 to the vehicle transmission, transaxle or driveshaft, thus producing either a single or 3-phase AC voltage, which is then amplified or "boosted" by a series of AC booster circuits 431-432 to the required higher AC voltage at a level of between 220V-400V or greater and at between 1 KW-10 KW volt/amp load in the Control Center Module 402 to produce a voltage that can be provided to the onboard charging system (OCU) 451 for storage onto the battery packs 452. This voltage is intended to be approximately equivalent to the voltage provided by a typical home charging system.

The control center 402 accepts a 12 VAC signal from the CORE components 401 that is generated from a mechanical link 411 to the vehicle that passes through a clutch 412 to a CORE generator 413. This input voltage from the generator 413 passes to a number of parallel signal paths to provide recharging voltage signals 434a-c that is used by an existing charging system 404 to recharge battery packs 452.

In a first signal path, the input voltage from the generator 413 is passed through a set of AC booster circuits 431-432 to convert the input voltage to a 120 VAC 434a and a 230/240 VAC 434b signals after passing through a current control circuit 433. The 120 VAC 434a and the 230/240 VAC 434b signals are connect to the selectable output 435. The AC booster circuits 431-432 are electronic components that, together, amplify or boost the incoming voltage signal to a higher level voltage (example: from 12V to 120V) capable of handling higher level currents (amperage). The current control circuit 443 is a part of the component makeup of the AC booster circuits 431-432 that facilitate the capacity to accommodate higher current flow, while not allowing current spikes and minimizing over-current situations.

A second signal path has the input signal from the generator 413 into an AC/DC rectifier circuit 441 to generate a 12V DC square wave signal that is input into a voltage regulator circuit 442. The output of the voltage regulator circuit 442 is input into an AC/DC inverter circuit 443 and an AC/DC amplifier circuit 444. The output of the AC/DC inverter circuit 443 is a 230/240 VAC signal connected to selectable output 434b. The output of the AC/DC amplifier circuit 444 is a 240/400 VDC square wave signal that is a third selectable output 434c. A set of solar panels 403 may also be used to input to the voltage regulator circuit 442. Only one of the signal paths 434a-c is connected to the selectable output 435 depending upon the requirements of an existing charging system 404.

The CCM MCU 421 is a Control Processor or CPU of the system. It will be of the latest/most advanced computer processors available at time of design finalization and build. Essentially, it is the computer that controls all the aspects of the CCM 402 and the CORE. The CCM MCU 421 controls all its functionality by running either it own proprietary software code or a combination of COTS and proprietary software, to provide this function. The Mode Select Switch dictates and changes the Operational Mode of the C.O.R.E. subsystems, as defined below:

An Off Mode disengages the CORE Clutch mechanism 412, thus shutting down the output voltages from the CORE Generator device, however still keeping the Control Center Module 442 and other subsystems powered and online, thus allowing for system operation, should mode selection change. The Off mode still allows for and does not impede external charging of the vehicle via external charging sources.

An ON Mode is a Default Mode if vehicle is NOT equipped with either a Secondary Battery Package or Solar Panels, or some other auxiliary input device.

ALL C.O.R.E. system and devices are powered on and operational, including the CORE Generator device and allows for raw output voltage from the CORE to the CCM.

This mode allows for Standard Operation while not providing for Supplemental input or Secondary/Redundant Battery operational control.

This is the Standard Mode if there are no other auxiliary devices attached, such as Solar Panels, or if the vehicle is only equipped with a single battery pack.

An AUTO Mode is used as the Default Mode if vehicle is equipped with either a Secondary Battery Array, Solar Panels, or other auxiliary device input.

ALL C.O.R.E. system and devices are powered on and operational and identical to ON Mode, with the added feature of provision for Supplemental input and/or Secondary/Redundant Battery operational control.

This mode allows for automatic battery changeover control, when a Secondary or Auxiliary Battery Array is installed.

This mode allows for Standard Operation while providing for Supplemental input to/from an installed Secondary or Redundant Battery Array or other auxiliary input.

This should be the Standard Mode if the vehicle is equipped with other Auxiliary devices attached, such as Solar Panels, or if the vehicle is equipped with multiple batteries or battery packs.

This mode can be used as a replacement Default Mode, in leu of using ON mode, whether or not, there are extra batteries or additional external auxiliary sources.

A Solar/EM Mode (emergency mode) is recommended only for driving or traffic situations where the vehicle encounters slower than normal driving conditions such as numerous stop-and-go situations or conditions like what may be encountered in heavily congested city driving or Emergency purposes only and should not be used as a primary mode of operation.

The Auxiliary inputs would supplement the charging system, although at dramatically decreased levels, due to the CORE Generator device not rotating in sufficient amounts to facilitate proper charging.

Figure 5:
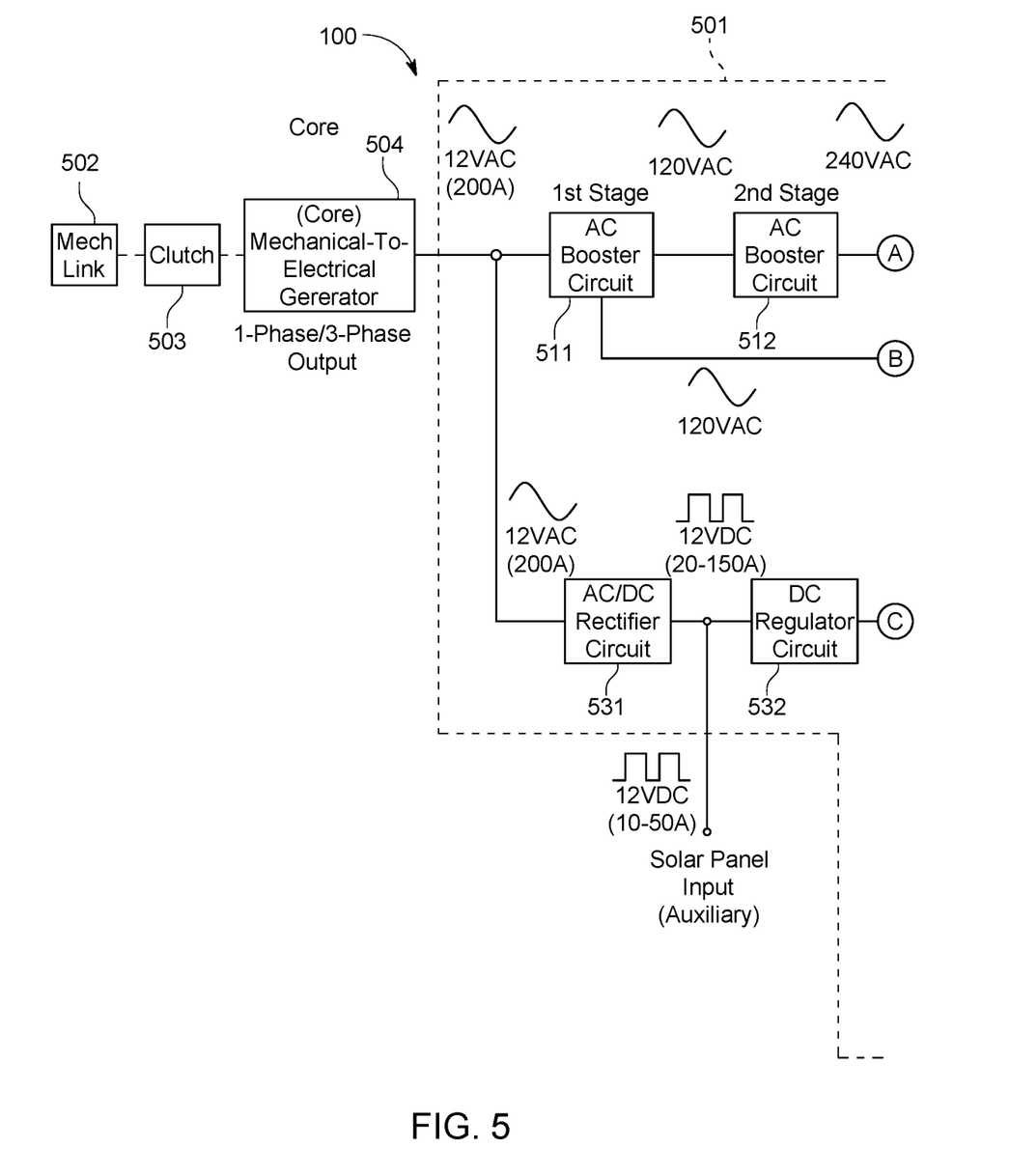
FIG. 5 illustrates a block diagram of electrical components of a control center that is part of an article of manufacture providing an onboard vehicle recharging environment according to the present invention.

FIG. 5 illustrates a block diagram of electrical components of a control center that is part of an article of manufacture providing an onboard vehicle recharging environment according to the present invention. FIG. 5 shows a second embodiment of a CORE system 100 that utilizes AC/DC conversion/inversion charging. In this second embodiment, a low voltage AC from the CORE device 504 is rectified, either through means of a built-in rectifier circuit 531 or through the rectifier circuits of the Control Center Module 301 then passed to the boost stage subsystem circuit(s) to amplify the DC voltage to a sufficient level to affect a nominal charge voltage, which then gets passed through the regulator subsystem 532 circuit, to regulate or maintain a constant voltage output regardless of motor, axle or transmission rotation speeds. Depending on the OEM requirements either AC or DC input charging voltage to the Onboard Charging Unit module 451 as shown in FIG. 4, the signal can be conditioned by either passing to the amplifier subsystem, for AC, or to the inverters subsystems 533, for DC voltages. The voltage may pass through several regulator and boost circuits 511-512 to produce the voltages and currents required, depending on manufacturer's specifications.

The boost stage is a series of regulator and/or inverter circuits designed to amplify the incoming voltage signal to appropriate level, of between 220V-400V or greater and between 1 KW-10 KW. This is to provide a charge level that the onboard charging unit 451 modules can accept and use to recharge the main batteries 452 as if the vehicle was plugged into an external charging device, while the vehicle is in motion.

The multiple signal paths generate a set of output signals including a 240 VAC signal 515, a 120 VAC signal 525, a 230/240 VAC 535, a 400 VDC signal 545, a 200 VAC signal 555. All PWR Contactors signals (515, 525, 535, 545 and 555), as shown in FIG. 5, can either be "manual" pass-thru devices, such as a voltage "jumper" or connection plug, or an electric/electronic pass-thru device, such as a voltage-controlled power contactor, that will either allow or prohibit voltages at certain output terminals. This is done as a safety feature, so that there will not be dangerous voltages present on any "unused" terminals, but only available on the selected/isolated output terminal.

The 240 VAC signal 515 is a 240 VAC "boosted" AC voltage, either Single-Phase or Three-Phased, developed from the raw AC voltage output of the CORE device (504). This voltage is then fed to the $1^{st}$, and then the $2^{nd}$ AC Boost Stage circuits (511-512), then delivered to the Regulator (513) and Current-Control Stage circuit(s) (514), which provides for a constant AC signal at varied rotational shaft speeds.

The 120 VAC signal 525 is a 120 VAC output of the $1^{st}$ AC Boost Stage circuit(s) (511) then delivered to the Regulator (521) and Current-Control (522) Stage circuit(s). This conditioned AC voltage is primarily for smaller EVs or HEVs, which only require standard household voltages for recharging. This would be equivalent to typical Level-1 Charging Stations. Typically, this will be a Single-Phase type of configuration, but can be modified to accommodate multiple-phased voltage signals.

The 230/240 VAC signal 535 is a 220-240 VAC "re-conditioned" AC voltage, derived from the AC/DC rectified (531) and regulated DC voltage output of the regulator circuit (532) and the High-Power Inverter (533) subsystem circuit. This conditioning stage utilizes a higher wattage/amperage subsystem to produce higher AC voltages, at higher amperage, generally required by Level-2 charging systems.

The 400 VDC signal 545 is a 400 VDC or "High-Voltage Fast Charge", where the output is derived from the AC/DC rectified (531) and regulated DC voltage output of the regulator circuit (532) is once again "boosted" in voltage level, multiple times, via Boost Stages (542) circuit subsystems, which amplify the DC signal to a level approximately equivalent to Level-3 or DC Fast Charge stations.

The 200 VAC signal 555 is a 200 VDC output is derived from the AC/DC rectified (531) and regulated DC voltage output of the regulator circuit (532) being fed to the 1st half of the High-Voltage Booster Stage (542), for vehicles requiring DC charging voltages, but not able to handle the High-Voltage Fast-Charge output. While this is still considered a DC Charging environment, it is more in line with Level-2 Charging Standard than the Level-3 Fast-Charge Standard.

While FIG. 4 shows an "overview of the voltage connections (CCM Output Terminals) and how/where it connects to the OEM integrated Onboard Charging system, FIG. 5 shows the CCM Output Terminals. FIG. 4 is an overview look at the CORE and CCM and how it connects to the vehicle systems, which could/may vary, and FIG. 5 is a more defined overview of just the CORE 401 and CCM 402.

Different OEMs have different Charge Port strategies the various signal paths show the generation of each signal with a selector to apply the appropriate charging signal for a particular vehicle. FIG. 4 shows two of the produced AC voltages taking a single path to the output connection terminals, which indicates just one possible embodiment to connect. In contrast, FIG. 5 shows the individual paths, which is another embodiment of output delivery. The CCM 402 will be flexible in how the connections can be made, due to possible changes/improvements in CCM circuit designs methodologies.

Even though particular combinations of features are recited in the present application, these combinations are not intended to limit the disclosure of the invention. In fact, many of these features may be combined in ways not specifically recited in this application. In other words, any of the features mentioned in this application may be included in this new invention in any combination or combinations to allow the functionality required for the desired operations.

No element, act, or instruction used in the present application should be construed as critical or essential to the invention unless explicitly described as such. Further, the phrase "based on" is intended to mean "based, at least in part, on" unless explicitly stated otherwise.

What is claimed is:

1. An article of manufacture providing an onboard vehicle recharging environment for a vehicle, the onboard vehicle recharging environment to be integrated into the vehicle, the onboard vehicle recharging environment comprises:

a voltage generator coupled by a mechanical device to rotating axle in the vehicle, the voltage generator generates a 12 VAC signal;

one or more voltage conversion signal path stages for converting the 12 V AC signal to an output power signal for coupling to an onboard battery recharging assembly of the vehicle to charge the vehicle onboard battery;

a memory having instructions stored thereon; and a control center processor having a processor configured to execute the instructions on the memory to cause the onboard vehicle recharging environment to operate is a plurality of operating modes, the operating modes comprise:

an Off Mode;

an. On Mode;

an Auto Mode; and a Solar/Emergency Mode (EM), the Solar/EM Mode being used when the vehicle encounters slower than normal driving conditions comprising numerous stop-and-go situations and conditions encountered in heavily congested city driving or Emergency purposes, and Auxiliary inputs supplement the charging environment, at decreased levels, due to a Continuous Onboard Recharging Environment Generator (CORE) device not rotating in sufficient amounts to facilitate proper charging.

2. The onboard vehicle recharging environment according claim 1, wherein the one or more voltage conversion signal path stages generate the output power signal for charging the vehicle onboard battery comprising:

a 120 VAC signal;
   a 230 VAC signal;
   a 240 VAC signal;
   a 200 VDC signal; and
   a 400 VDC signal.

3. The onboard vehicle recharging environment according claim 1, wherein the onboard vehicle recharging environment further comprises a clutch device between the voltage generator and a mechanical device coupled to the vehicle axle.

4. The onboard vehicle recharging environment according claim 3, wherein the mechanical device comprises one of the following: a belt/pully connection to a vehicle transaxle, a belt/pully connection to a vehicle driveshaft, a direct connection to a vehicle transaxle, and a direct connection to a vehicle driveshaft.

5. The onboard vehicle recharging environment according claim 1, wherein the off mode disengages a clutch to shut down the output power signal from the voltage generator.

6. The onboard vehicle recharging environment according claim 5, wherein, the off mode keeps the control center processor powered and online to allow for operation when the operating mode changes.

7. The onboard vehicle recharging environment according claim 1, wherein the on mode is the default mode for vehicles that are not equipped with a secondary battery package a solar panels, and an auxiliary input device.

8. The onboard vehicle recharging environment according claim 1, wherein the auto anode is used as the default mode if vehicle is equipped with either a Secondary Battery Array, Solar Panels, or other auxiliary device input.

9. The onboard vehicle recharging environment according claim 1, wherein the Solar/EM Mode is used for driving or traffic situations where the vehicle encounters slower than normal driving, numerous stop-and-go conditions and heavily congested city driving conditions.

10. The onboard vehicle recharging environment according claim 1, wherein the vehicle comprises a hybrid electrical-combustion engine and an electrical vehicle.

* * * * *